US012551364B2

(12) United States Patent
Watabe et al.

(10) Patent No.: US 12,551,364 B2
(45) Date of Patent: Feb. 17, 2026

(54) ORTHOPEDIC WALKING BOOT

(71) Applicant: Ortho Systems, Agoura Hills, CA (US)

(72) Inventors: Kenji Watabe, Ventura, CA (US); Tracy E. Grim, Thousand Oaks, CA (US); Edwin Erwin, Studio City, CA (US); Zhaung Shao, Canoga Park, CA (US)

(73) Assignee: Ortho Systems, Agoura Hills, CA (US)

( * ) Notice: Subject to any disclaimer, the term of this patent is extended or adjusted under 35 U.S.C. 154(b) by 141 days.

(21) Appl. No.: 18/369,066

(22) Filed: Sep. 15, 2023

(65) Prior Publication Data

US 2024/0091042 A1 Mar. 21, 2024

Related U.S. Application Data

(60) Provisional application No. 63/407,784, filed on Sep. 19, 2022.

(51) Int. Cl.

| | |
|---|---|
| ***A61F 5/01*** | (2006.01) |
| *A43B 7/1485* | (2022.01) |
| *A43B 7/32* | (2006.01) |
| *A43B 13/18* | (2006.01) |

(52) U.S. Cl.
CPC .......... *A61F 5/0195* (2013.01); *A61F 5/0111* (2013.01); *A43B 7/1485* (2013.01); *A43B 7/32* (2013.01); *A43B 13/183* (2013.01)

(58) Field of Classification Search
CPC .... A61F 5/0111; A61F 5/0113; A61F 5/0127; A61F 5/0195; A43B 7/144; A43B 7/1485; A43B 7/32; A43B 13/183; A43B 21/26; A43B 21/32
See application file for complete search history.

(56) References Cited

U.S. PATENT DOCUMENTS 5,381,608 A * 1/1995 Claveria .............. A43B 13/183 36/35 R
5,857,987 A * 1/1999 Habermeyer ......... A61F 5/0127 36/118.2
6,155,998 A * 12/2000 Gilmour ................... A61F 5/14 36/95
7,249,425 B2 * 7/2007 Wang ..................... A43B 7/144 36/44
8,932,245 B2 * 1/2015 Chen ..................... A61F 5/0195 602/5
9,668,907 B2 * 6/2017 Romo ..................... A61F 5/012
(Continued)

*Primary Examiner* — Keri J Nelson
(74) *Attorney, Agent, or Firm* — Fulwider Patton LLP

(57) ABSTRACT

An orthopedic walker is disclosed that improves comfort and shock absorption during use by incorporating a flexure zone that deflects to ease the forces caused by the heel strike portion of a patient's gait. The flexure zone is created by cutting around the heel on the bottom of the sole to allow for the heel portion to flex. The exterior shell of the walker is may be made of a formable resilient material that when combined with an attached tongue structure reduces a volume of encapsulation of the lower limb. The shell encloses a padding on the inner side that may take the form of air/bladders and/or foam, and tabs on each side selectively engage receiving tabs on the inside lateral and medial side of the base upright portions. A separate tongue structure is used to enclose the foot and is made adjustable using various methods such as slits and novel connectors.

8 Claims, 7 Drawing Sheets

(56) References Cited

U.S. PATENT DOCUMENTS

| | | | | |
|---|---|---|---|---|
| 9,943,432 | B1 * | 4/2018 | Butler | A61F 5/0127 |
| 10,441,021 | B1 * | 10/2019 | Polk | A43B 3/12 |
| 2006/0174515 | A1 * | 8/2006 | Wilkinson | A43B 21/32<br>36/27 |
| 2009/0287127 | A1 * | 11/2009 | Hu | A61F 5/0111<br>602/27 |
| 2015/0047224 | A1 * | 2/2015 | Zhao | A43B 13/223<br>36/28 |
| 2017/0056230 | A1 * | 3/2017 | Miller | A61F 5/0127 |
| 2020/0154820 | A9 * | 5/2020 | Norton | A43B 13/183 |

* cited by examiner

ORTHOPEDIC WALKING BOOT

CROSS-REFERENCES TO RELATED APPLICATIONS

This application claims priority to U.S. Provisional Patent Application No. 63/407,784, filed Sep. 19, 2022, the content of which is incorporated by reference herein in its entirety.

BACKGROUND

It is common that people, especially active and/or frail people, experience a variety of lower leg and ankle injuries. To aid in the treatment of the injuries it is desirable to immobilize the injury, typically above and below the effected joint. Physicians traditionally will place patients in a cast that will start at the toes and ends below the knee in what is called a short leg cast. Patients have complained that casts are hot, promote skin itching and will rub the leg when the swelling subsides.

An alternative to the short leg cast is what is referred to in the industry as a short leg walker, a device that is made of a rigid plastic frame lined with a soft padding to accommodate the leg comfortably. Many times the liner, or "soft good," may incorporate an air bladder that is adjusted by the patient to improve the fit and help limit swelling, resulting in less pain and more stability. These walkers can be easily removed for bathing, for suture removal, and for conducting passive range of motion (ROM) exercises.

Walkers have historically been intentionally rigid, immobilizing the foot and ankle at a neutral position (e.g., 90 degrees). The patient can walk normally when the ankle is held at 90 degrees and this prevents the patient from undue impact on the toes or on the heel. The outer sole is usually rounded from front to back in a rocking chair type configuration to initiate a smoother stride from front to back, promoting an initial heel strike, transitioning the weight as the foot is rocked from back to front, leading to a toe-off for a successful step. However, improving the shock absorbing aspects of the orthopedic walkers is an ongoing goal, since any impact on an injured leg becomes magnified.

U.S. Pat. No. 5,464,385 to Grim teaches a lightweight walker with an open heel. The Grim device provides a shock absorbing element located at the heel strike portion to reduce the amount of impact to the leg while walking. The leg walker of Grim also includes a small, lightweight and removable inner ankle "bootie" brace that can be removed from the leg walker and worn separately to bed. When the ankle bootie is separately worn, it is capable of effectively stabilizing and supporting injuries to the lower leg extremities, adjacent to the ankle, while affording the patient a comfortable night's sleep.

U.S. Pat. No. 6,027,468 to Pick also discloses an orthopedic walker purporting to reduce shock absorption. The brace comprises a leg portion adapted to fit substantially around the lower leg of a patient, and a sole portion that fits beneath the patient's foot. The lower surface of the sole is provided with a layer of a durable shock-absorbing material. The sole portion of the walking brace is provided with an opening in the area of the patient's heel and the layer of shock-absorbing material includes a heel portion which extends upwardly through the opening in the sole portion. Thus, when the patient stands or walks, the patient's heel impacts the resilient shock absorbing material of the heel portion while the rest of the patient's foot engages the rigid upper surface of the sole portion.

The present invention provides improvements over the prior art that result in a novel, safer orthopedic walker.

SUMMARY OF THE INVENTION

The present invention relates to a circumferential walker having new features that improve the design, comfort and function of a short leg walking device. Orthopedic walking boots, or "walkers," and other short leg walking boots designs have tried to reduce the shock during the heel strike portion of the patient's gait. The intent of a short leg walking boot is to allow immobility of the lower limb during ambulation while keeping the normal gait intact rather than walking with a pronounced limp that could lead to subsequent injuries to the non-affected leg and hip. Having a shock absorption feature also assists in reducing bruising of the heel since a walking boot must be made of rigid materials to be able to keep the lower leg fixed as well as to bear the weight of the patient during use. Rocker bottom soles have been used in short leg walking boots for many years with good results on reducing peak and shear forces within the walking boot during ambulation.

To improve the shock absorption characteristics of the present invention, a flexure zone is created by cutting around the heel on the bottom of the sole to allow for the heel portion to flex during heel strike. The flexure zone is connected to the sole along a transverse edge adjacent the midfoot area, such that the cut out area forms a cantilever spring-like mechanism that flexes during heel strike.

The present invention also preferably includes a curved outer sole that allows for full gait from heel strike to toe off so that the wearer may stride through his/her gait fluidly. The curvature of the sole corresponds to a preferred arc radius for the length of the sole, and this radius has been demonstrated to reduce peak forces during a ambulation.

The exterior shell of the walker is may be made of a formable resilient material that when combined with an attached tongue structure reduces a volume of encapsulation of the lower limb. The anterior shell may be made of a semi-rigid, yet flexible, material that can be formed to fit a specific anatomy of the anterior lower limb. The shell encloses a padding on the inner side that may take the form of air/bladders and/or foam, and tabs on each side selectively engage receiving tabs on the inside lateral and medial side of the base upright portions.

In one preferred embodiment of the invention, thermal channels are vertically incorporated on the inner surface of the posterior base and on the inner surface of the exterior shell. An outsole may be added with different types of spring resistors underneath the heel flexure zone to limit the amount of flex and/or reduce the impact during heel strike. Certain sole geometry other than columns can be used to effect heel strike dampening as well.

DETAILED DESCRIPTION OF THE PREFERRED EMBODIMENTS

Figure 1:
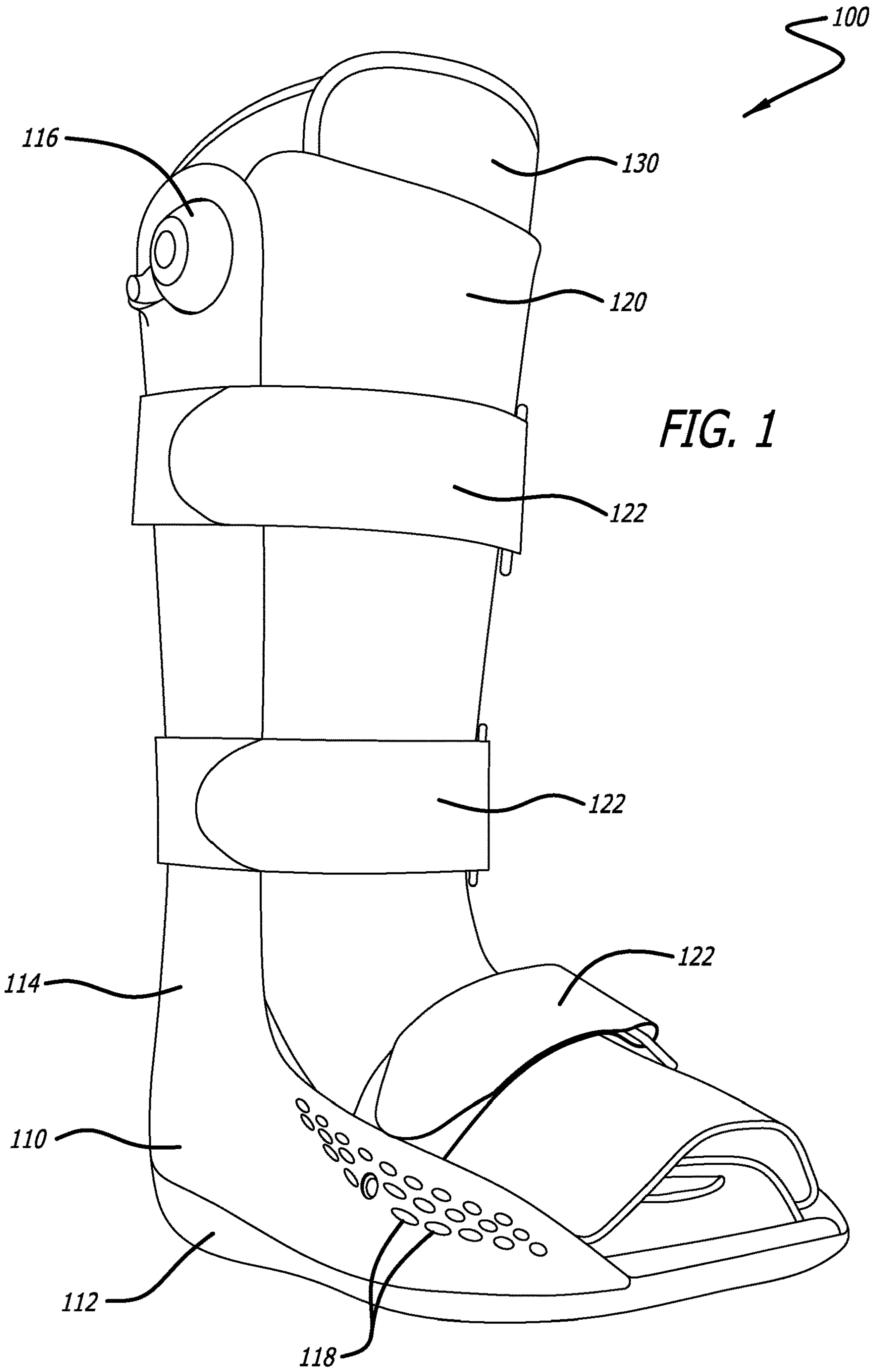
FIG. 1 is an elevated, perspective view of a first embodiment of the present invention.

The flex zone of the present invention is designed to reduce the impact of the heel when walking. The flex zone makes use of a cantilever spring design on the inner sole surface below the heel. The heel of the patient engages the flex zone during the heel strike portion of the patient's gait reducing impact by absorbing energy upon impact and then returning energy back to the heel through mid-stride of the patient's gait enabling the patient into a proper toe-off and normal gait. As the heel bears against the flex zone, a plate attached at or near the midfoot deflects downward, allowing a more gradual deflection. This plate acts like a cantilever beam in which deflection versus force is a second order equation. The amount of deflection is determine by several factors, including the cross sectional area (width and thickness) of the cantilever base section, the length of the cantilever, the stiffness of the material used, and the firmness of the underlying material of the outsole that will resist deflection of the cantilever.

The cantilevered heel sections can take various shapes, such as semi-circular or semi-octagonal, and are formed by cutting the upper sole around the heel area. The length of the cantilevered heel section can differ depending upon the needs of the patient and the other materials. However, the cantilevered heel section is displaced downward when the heel strikes the upper surface of the sole, and the heel section snaps upward as the heel is lifted during the "toe off" phase of the gait. In this manner, the impact is greatly reduced while the springboard effect of the upward response improves the patient's ability to walk.

In combination with the cantilevered heel portion, the outsole of the walker base may have a shock absorption zone beneath the cantilevered heel portion that works in concert with the heel flex zone. The shock absorption zone can take different forms, such as columns or fingers that protrude upward toward the heel flex zone and act to dampen the impact of the heel strike. The shock absorbers resist the compression of the cantilever heel and can be designed to engage at a certain deflection and decelerate the flexure of the heel at a given rate to optimize the damping process.

Another feature of the present invention is the incorporation of elongate apertures along the posterior support. A major concern for these types of walkers is the buildup of heat since the lower limb is typically wrapped with a softgood made of foam and fabric material. This padding is then encapsulating by the outer shell, resulting in considerable heat accumulation. The present invention makes use of thermal channels as well as ventilation holes to allow heat to escape during use. The ventilation is achieved by elongate openings, e.g. ovals, extending up the back of the walker. Additional openings are located along the Achilles tendons and on the peripheral edges of the foot portion. In a preferred embodiment, the openings are laser cut to produce a pattern of openings that is aesthetically pleasing and retains the majority of the walker's strength at these locations.

Another feature of the present invention is a calf relief region that prevents the posterior portion of the walker from digging into and causing discomfort to the patient's calf. The calf relief region includes a thinner section to provide more room for the calf. Alternatively, the thinner section can be replaced with a soft pad that yields to prevent the walker from digging into the patient's calf. The thinning of the posterior wall allows the walker to expand slightly and provide additional comfort to the patient.

The outer shell can be combined with a softgood inner bootie or liner for comfort. The bootie can be worn at night to bed without the hard shell, and can have multiple layers or densities. This allows the liner to replace a fixed padding or foam liner on the shell.

Another feature of the present invention is a hinged anterior tongue member that is connected to the shell near the toe. The hinge can be formed with an elastic component, or part of the softgood may operate as the hinge. The hinged anterior tongue can have its own padding, and can be used with or without traditional closing flaps attached to the softgood. The benefit of the hinged tongue is that it allows the anterior shell to pivot as one piece away from the user when donning and doffing the product without separating from the anterior shell. The pivoting at either end automatically aligns and positions the anterior shell when applying. The combination of the hinged anterior shell and a continuous padding offers a more uniform support for the patient.

The combination of the hinged anterior shell with an "X"-shaped attachment offers extra rigidity and support when applying the anterior shell, wearing (preventing unwanted movement), and support when taking the walker off the leg. The hinged anterior shell allows quick access to the dorsum of the foot and expedites release and application of the brace. That is, it allows the patient to easily take off the walker without needing to open a separate toe flap. Figure X shows the X shaped attachment connecting the anterior tongue to the shell, and the X shaped attachment in combination with a buckle.

The X shaped attachment provides an adjustment mechanism that adapts to different sizes and shapes of lower extremities. The adjustable X brace rotates and adapts to the patient's anatomy. It can be attached at the shell edges and flex or twist slightly to accommodate the movements of the lower leg. The connector also provides clearance for the sensitive area of dorsum of forefoot. It is useful to distribute load evenly across the ankle forefoot area, and apply load in specific beneficial areas. It can also be helpful in keeping the heel back during dorsiflexion.

Figure 2:
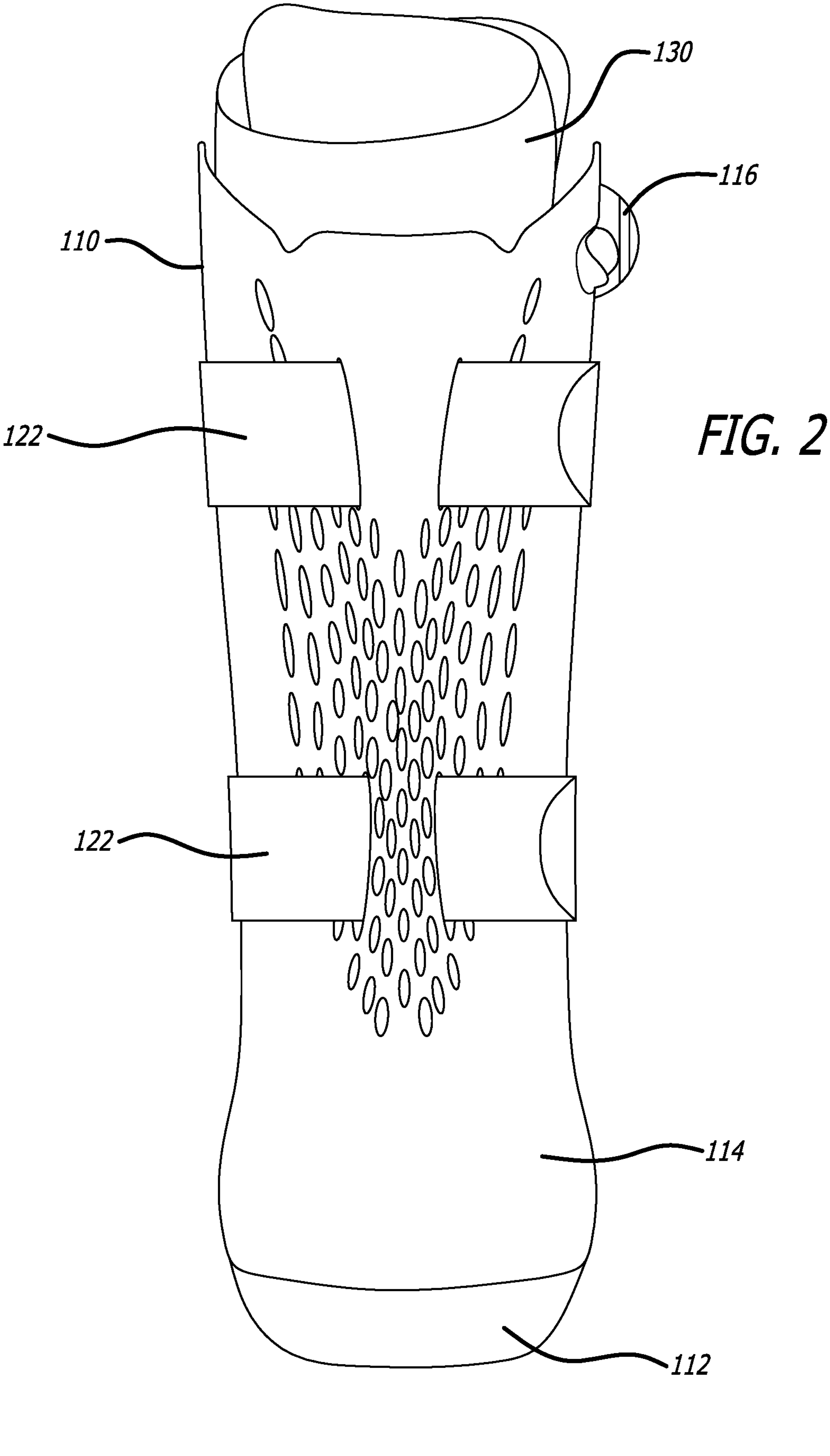
FIG. 2 is a rear view of the back side of the walker of FIG. 1.

FIG. 1 illustrates a first embodiment of the present invention in the form of a circumferential walker 100 having new features that improve the design, comfort and function of a short leg walking device. The walker 100 includes a shell 110 that has a molded sole 112 and a vertical calf support 114, but is open on the anterior portion of the foot. A separate tongue 120 is used to close the walker and compress the patient's foot using straps 122 that wrap around both the shell 110 and the tongue 120. Inside the cavity formed by the shell/tongue combination is a padded softgood 130 that protects the foot. In some embodiments, the softgood may include a bladder that is pumped with air using the pump button 116 to adjust the fit of the walker to different size feet and provide in further refinement in the fit of the softgood 130. To dissipate heat, the shell can be provided with elongate laser cut apertures 118 at the instep and or Achilles to aid in dissipating the buildup of head inside the walker 100. FIG. 2 shows additional apertures 119 to release the heat stored in the calf area of the walker.

Figure 3:
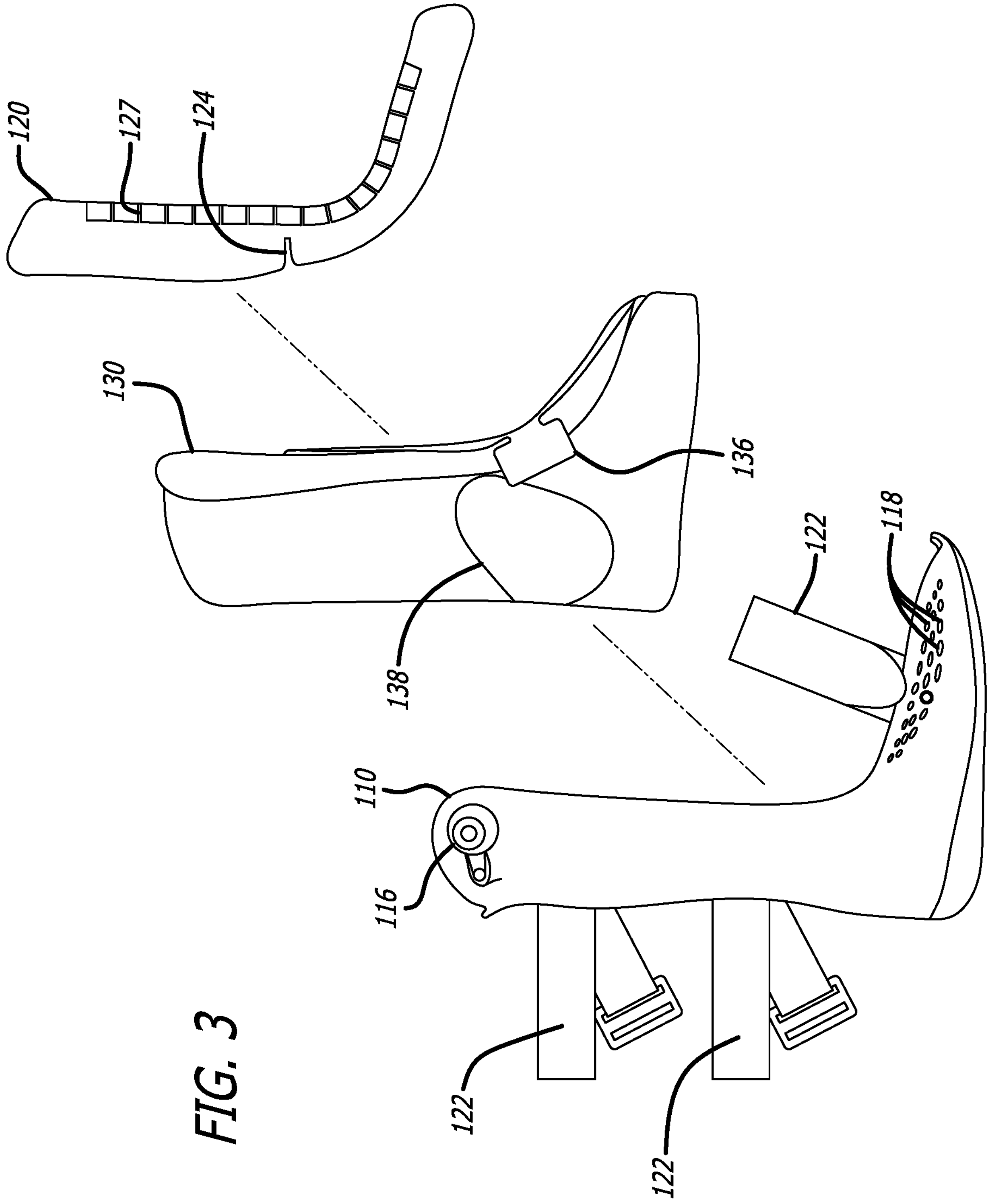
FIG. 3 is a an exploded view of the shell, softgood, and tongue of the walker of FIG. 1.

FIG. 3 shows the shell 110, tongue 120, and softgood 130 of the walker 100. The patient can first don the softgood 130, which may be secured by a flap 136 and may include a bladder 138, and worn like a sock to bed or when the ambulatory portion of the walker is not needed. To add the shell 110, the patient steps into the shell 110, and places the tongue 120 over the foot at the open portion of the shell. Straps 122 are then used to compress the foot, reduce the volume of the walker, and tighten the device onto the patient's foot. The tongue 120 may include lateral slits 124 to provide some flex to the tongue and avoid discomfort due to the tongue being too stiff or ill fitting. The upper surface may also be formed with ribs 127 separated by grooves to further increase flexibility. Once the walker is assembled, the pump button 116 can be used to inflate the bladder 138 to further adjust the fit and compression of the softgood on the patient's foot.

The present inventors noted that current circumferential walker designs fail to properly lock the lower limb into the walker base. The main purpose of a circumferential walker is to mimic and short leg cast, but current circumferential walkers in the market make use of a thin anterior shell that does a poor job of providing anterior control of the lower limb. To address this problem, the tongue 120 of the current invention utilizes the natural anatomical shape of the anterior lower limb and dorsum of the foot to establish a molded panel that fits snuggly and contours to the shape of the front part of the lower leg, ankle and foot when applied to the user. The anatomical shape allows the tongue 120 to come into contact with the entire adjoining surface of the lower leg and foot and, in doing so, creates greater purchase of the tongue 120 to the limb for increased support and locks the circumferential walker to the foot. In doing so the circumferential walker fits more like a custom applied cast than a prefabricated lower limb orthosis.

This same embodiment can be made with different materials from an EVA closed cell foam to an open cell foam with rigid structural stiffeners that are attached to the outer portion of the anterior panel. Certain material types like rigid EVA foams can be trimmed by the practitioner for an even more custom fit for certain anatomies.

Figure 4:
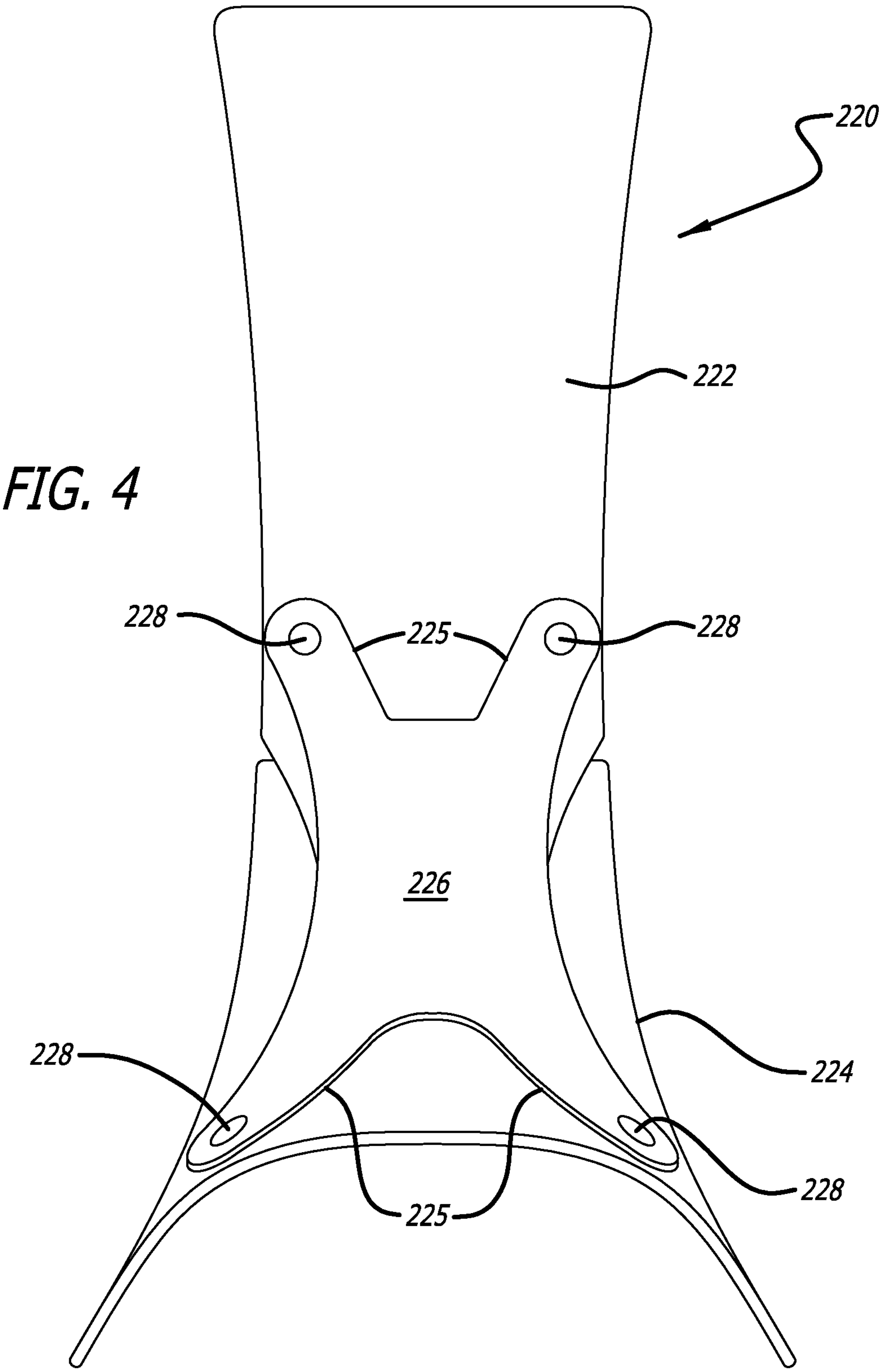
FIG. 4 is a front view of an X connector that couples an upper portion of the tongue to a lower portion.
Figure 5:
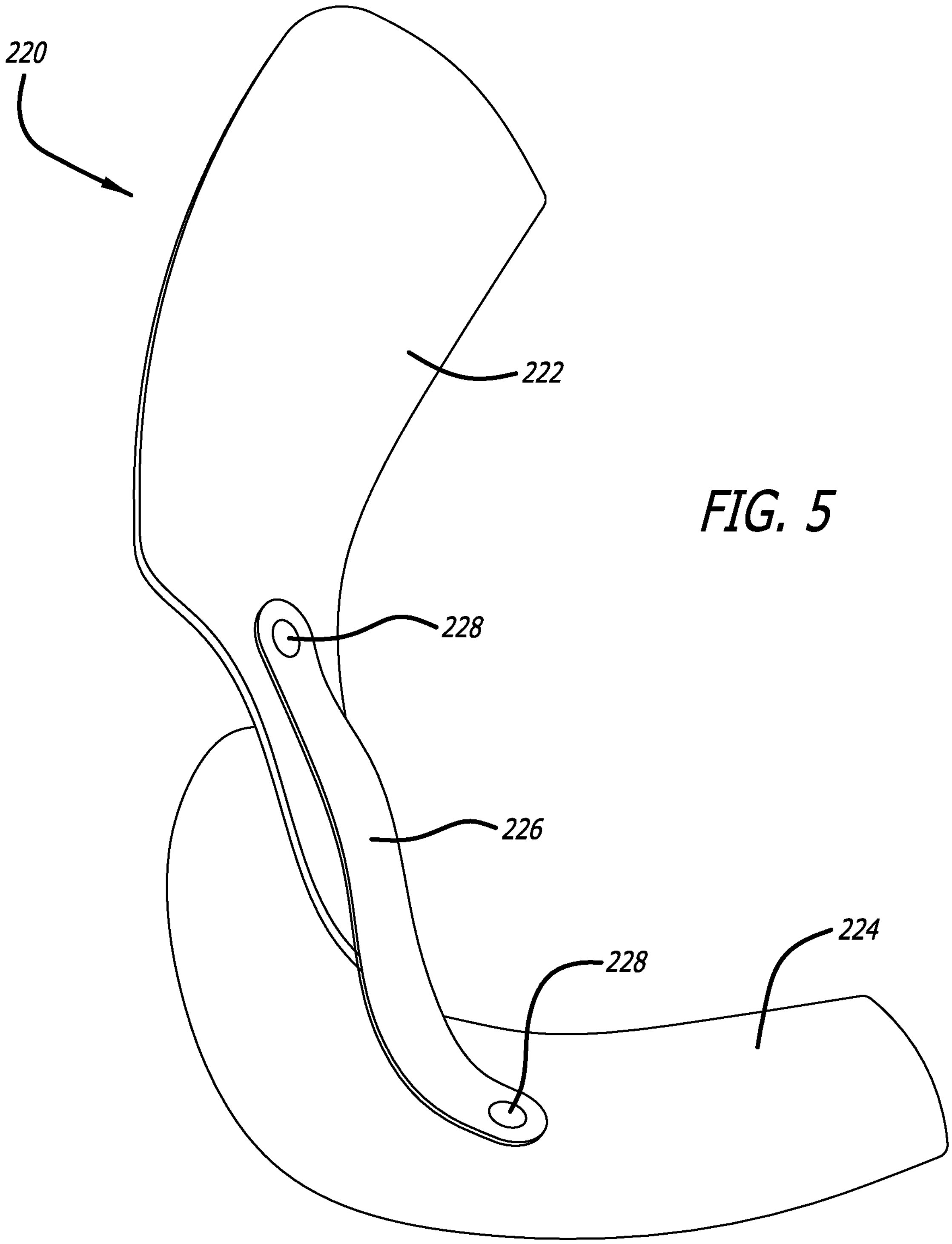
FIG. 5 is a side view of the tongue of FIG. 4.

FIGS. 4 and 5 illustrate a three piece tongue 220 tongue that has an upper parabolic shell 222 and lower parabolic shell 224, and an "X" shaped spring connector 226 that connects the upper and lower sections via rivets 228 and helps distribute a load to the upper and lower shells when a dorsal strap is engaged on top of the tongue 220. The X-shaped spring connector 226 includes four projections 225, two each connecting the upper parabolic shell 222 and lower parabolic shell 224. This connector provides a pivot that adjusts to variances in the shape of the patient's foot for greater comfort and support of the limb. Another embodiment is of a similar shaped anterior panel, but has specific locations that have been compressed further to allow for proper forming around the anterior lower limb. The knocked down portions allow the compressed semi rigid material to easily conform and contour to different anatomies.

Figure 6:
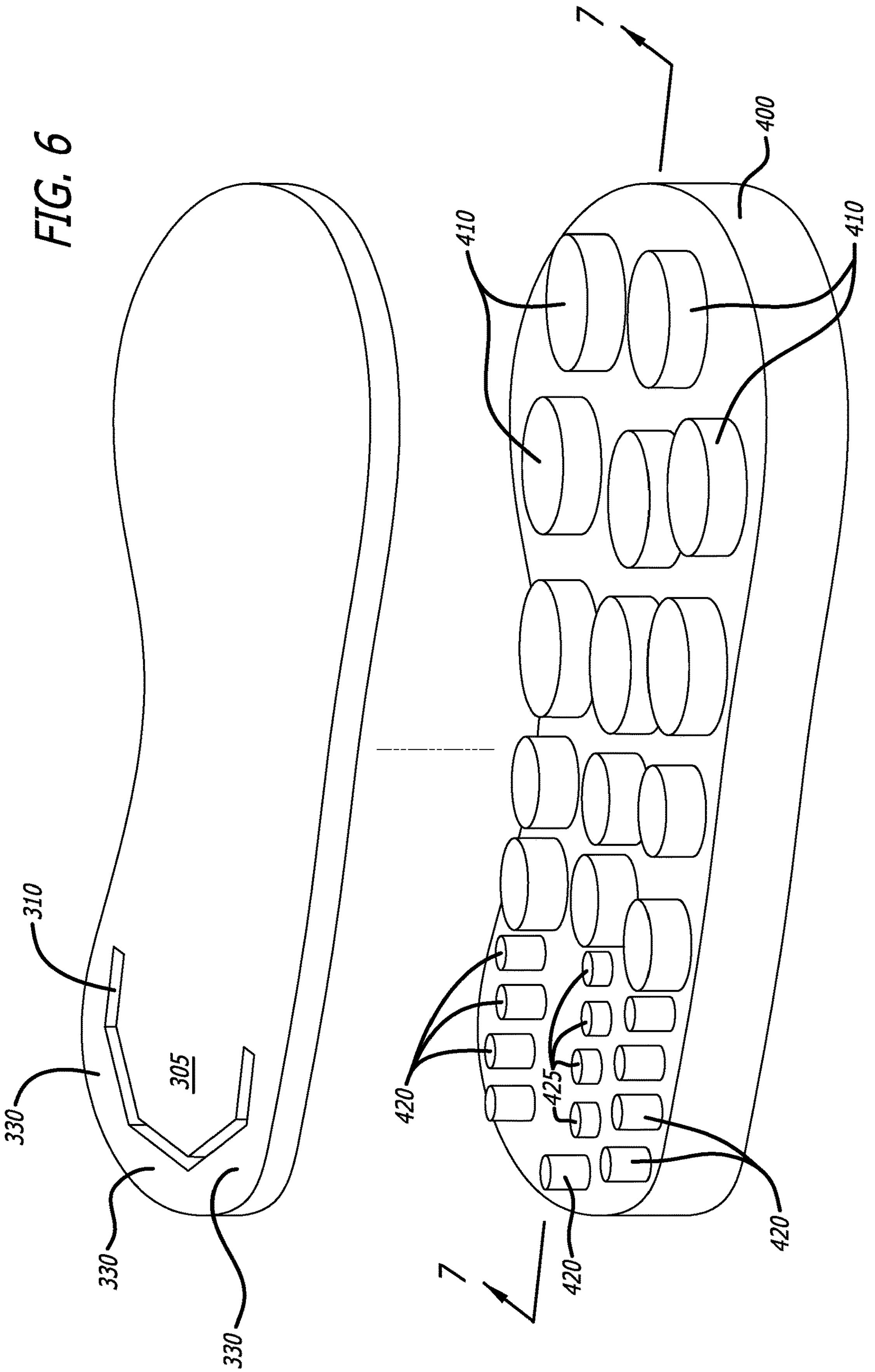
FIG. 6 is an exploded view of the upper sole and lower sole sandwiching columnar absorbers.
Figure 8:
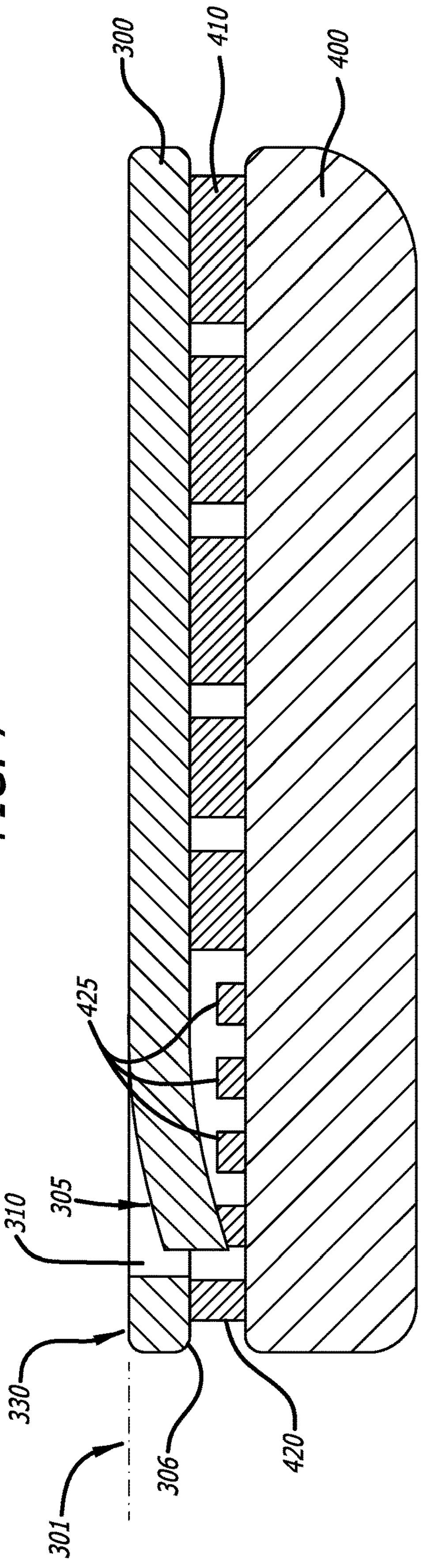
FIG. 8 is a cross-sectional view of a deflection of the cantilevered sole against the absorbing columns.

FIG. 6 illustrates a flex zone that is designed to reduce the impact of the heel when walking. The flex zone makes use of a cantilever spring design on the inner sole 300 below the patient's heel (i.e., above a heel portion 405 of the outer sole). A portion of the inner sole 300 is cut to form an elongate slit 310 in the shape of a semi-octagonal (see FIG. 6), semi-circular, or the like so as to create a portion of the sole that yields when acted upon by a force such as the weight of the patient during the heel strike phase of the gait. As the patient's heel impacts the flex zone 305 during impact, the force applied by the foot on the inner sole 300 at the flex zone causes the flex zone 305 to deflect below the horizontal plane 301 as shown in FIG. 8. This deflection of the flex zone 305 reduces the impact felt by the patient, which in turn leads to greater comfort and improved walking conditions. It must be remembered that injuries that necessitate the use of walkers such as the present invention typically are accompanied by significant pain to any undue force or impact. This flex zone and the relief it offers the patient can lead to better mobility, increased tendency to wear the device, and less stress-related recovery delays. Here, the heel of the patient engages the flex zone 305 during the heel strike portion of the patient's gait reducing impact by absorbing energy upon impact and then returning energy back to the heel through mid-stride of the patient's gait enabling the patient into a proper toe-off and normal gait.

The deflection of the flex zone 305 contrasts with portion 330 of the inner sole that is supported by the more rigid columns 420 and does not deflect when the force is applied to the flex zone 304. Rather, the portions 330 form a structure that cradles the calcaneus as the flex zone deflects, which in turn both supports the rear portion of the foot and resists undesirable sliding of the foot inside the walker during heel strike. FIG. 6 shows how the elongate slit 310 outlines the shape of the patient's heel to permit both the deflection of the flex zone 305 and the cradling of the calcaneus as described above.

The flex zone simulates a cantilever beam having a spring constant that is determined by several factors, including the cross sectional area (width and thickness) of the cantilever base section (bend location), the length of the cantilever from bend location to the point of the applied force (heel strike location), the stiffness of the material used, and the firmness of the underlying material of the outsole that will resist deflection of the cantilever.

Figure 7:
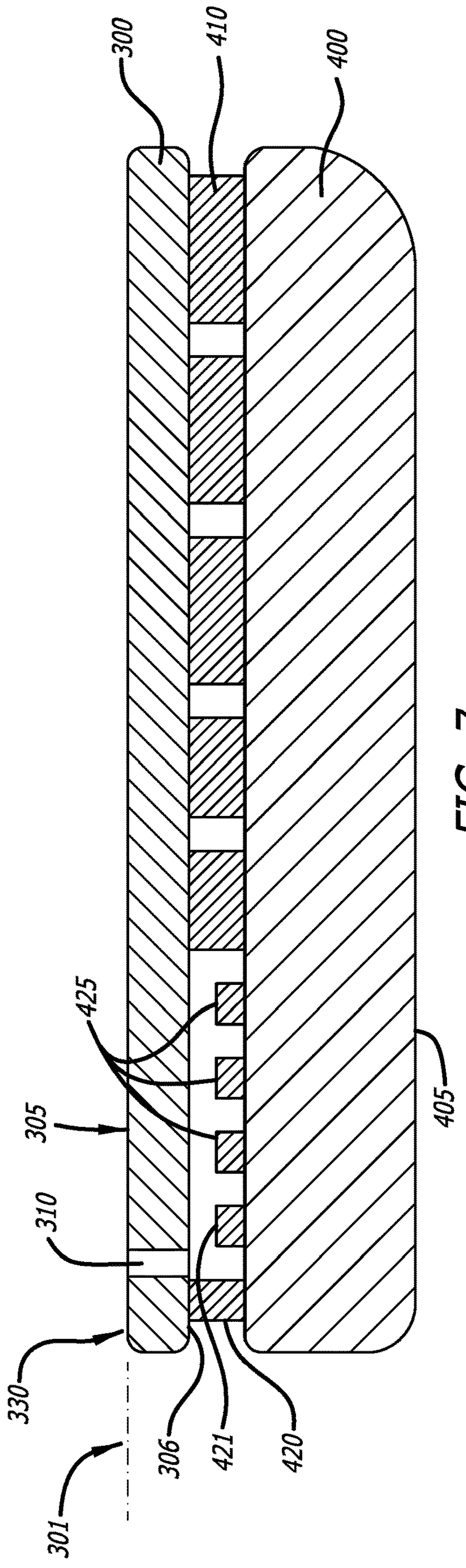
FIG. 7 is a cross-sectional view of the cantilevered sole.

The inner sole 300 typically is seated on the walker's outer sole 400, which may be separated by pads 410 disposed between the inner and outer soles. To even further soften the impact of the heel strike, the outer sole 400 may be formed with a plurality of resilient columns 425 below the flex zone 305 such that the resilient columns 425 have an upper surface 421 situated below the lower surface 306 of the inner sole (see FIG. 7). When the flex zone 305 deflects, at a certain point it makes contact with the absorption columns 425 to slow the acceleration of the flex zone and reduce stresses further. The columns 425 can also aid in the reflex of the flex zone upward upon release of the weight of the patient to improve the natura push off of the patient's gait.

While various embodiments have been described and depicted above and in the drawings, it is to be understood that the invention is not limited strictly to those embodiments depicted and described. Rather, one of ordinary skill in the art will readily recognize and appreciate various modifications and substitutions, and the breadth of the invention is intended to include all such modifications and substitutions. Therefore, the scope of the invention is properly governed by the words of the appended claims, given their customary and ordinary meanings, without implicating 35 USC Section 112(6), consistent with but not limited to the foregoing descriptions and depictions.

We claim:

1. An orthopedic walking boot, comprising:

a shell having a molded lower surface and a vertical calf support;

a removable tongue adapted to cooperate with the shell to form a closed space, said removable tongue comprising:

an upper parabolic panel;

a lower parabolic panel disposed behind the upper parabolic panel such that portions of the upper parabolic panel and lower parabolic panes overlap;

an X-shaped connector having a body, two upwardly extending projections and two downwardly extending projections; and a first pair of fasteners rigidly connecting the X-shaped connector to the upper parabolic panel at the two upwardly extending projections, and a second pair of fasteners rigidly connecting the X-shaped connector to the lower parabolic panel;

a softgood configured to be worn over a patient's foot and disposed within the shell;

straps for securing the removable tongue portion to the shell; and an inner sole within the shell generally defining an a horizontal plane at an upper surface, and a cantilevered portion disposed above a heel of the shell, the cantilevered portion defined by an elongate slit in the inner sole that extends partially around the heel;

whereby the cantilevered portion is configured to deflect below the horizontal plane when a force applied in a heel strike phase of a user's gait.

2. The orthopedic walking boot of claim 1, wherein the shell includes elongate apertures formed on a rear surface configured to release heat from the walking boot.

3. The orthopedic walking boot of claim 2, further comprising elongate apertures on side surfaces of the shell configured to release heat from the walking boot.

4. The orthopedic walking boot of claim 1, wherein the elongate slit is cut in a shape of a semi-octagon.

5. The orthopedic walking boot of claim 1, wherein the elongate slit is cut in a shape of a semi-circle.

6. The orthopedic walking boot of claim 1, further comprising a plurality of force absorbing columns spaced from and below the cantilevered portion of the inner sole, said force absorbing columns positioned to make contact with a lower surface of the cantilevered portion when a force is applied to the cantilevered portion.

7. The orthopedic walking boot of claim 1, wherein the removable tongue portion includes lateral slits on each side.

8. The orthopedic walking boot of claim 7, further comprising ribs formed on an upper surface of the removable tongue portion.

* * * * *